United States Patent
Chadwick

(10) Patent No.: US 7,657,320 B2
(45) Date of Patent: Feb. 2, 2010

(54) ELECTRONIC DEVICE WITH DUAL PURPOSE INDUCTIVE ELEMENT

(75) Inventor: Peter Edward Chadwick, Swindon (GB)

(73) Assignee: Zarlink Semiconductor AB (SE)

( * ) Notice: Subject to any disclaimer, the term of this patent is extended or adjusted under 35 U.S.C. 154(b) by 527 days.

(21) Appl. No.: 11/463,484

(22) Filed: Aug. 9, 2006

(65) Prior Publication Data
US 2008/0039903 A1    Feb. 14, 2008

(30) Foreign Application Priority Data
Aug. 16, 2005    (GB) ................... 0516778.8

(51) Int. Cl.
*A61N 1/00* (2006.01)

(52) U.S. Cl. ...................................... 607/60

(58) Field of Classification Search .............. 607/60; 600/549, 561; 455/127.1, 572; 136/246; 290/1 A; 307/66; 315/247, 291, 308, 312; 322/24, 28; 323/222–226, 235, 237, 247, 323/255, 283; 330/123, 126

See application file for complete search history.

(56) References Cited

U.S. PATENT DOCUMENTS

| | | | |
|---|---|---|---|
| 4,561,443 A | | 12/1985 | Hogrefe et al. |
| 4,918,745 A | | 4/1990 | Hutchison |
| 5,235,980 A | | 8/1993 | Varrichio et al. |
| 5,654,881 A | * | 8/1997 | Albrecht et al. ............ 363/25 |
| 6,340,931 B1 | * | 1/2002 | Harrison et al. .......... 340/572.1 |
| 6,731,976 B2 | * | 5/2004 | Penn et al. ................. 600/544 |
| 2004/0113790 A1 | | 6/2004 | Hamel et al. |
| 2005/0264271 A1 | * | 12/2005 | Lam et al. ................. 323/282 |
| 2005/0267550 A1 | | 12/2005 | Hess et al. |
| 2005/0283207 A1 | | 12/2005 | Hochmair et al. |
| 2007/0178857 A1 | * | 8/2007 | Greene et al. ............ 455/127.1 |
| 2007/0281755 A1 | * | 12/2007 | Dwelley ..................... 455/572 |

FOREIGN PATENT DOCUMENTS

| | | |
|---|---|---|
| EP | 0 697 900 B1 | 6/2000 |
| FR | 1.208.864 A | 2/1960 |
| FR | 2 657 479 A1 | 7/1991 |

* cited by examiner

*Primary Examiner*—George Manuel
*Assistant Examiner*—Robert N Wieland
(74) *Attorney, Agent, or Firm*—Lawrence E. Laubscher, Jr.

(57) ABSTRACT

Disclosed is an electronic device comprising an inductive element configured to function in a communication mode as an antenna for picking up communication signals, and in a power conversion mode as an inductive element configured to be the energy storage inductor in a switching regulator used for conditioning the power available from an internal power source to power for powering the device, and a controllable switch for switching between said communication mode and said power conversion mode. The communications system further comprises a controllable switch for connecting said inductive element to either said receiver or said power conversion circuit. The controllable switch switches the system between the communication mode and the power conversion mode by means of unipolar or bipolar transistor switches or by mechanical switches or relays. The communication system may be used in an in-vivo medical device.

3 Claims, 1 Drawing Sheet

ELECTRONIC DEVICE WITH DUAL PURPOSE INDUCTIVE ELEMENT

FIELD OF THE INVENTION

The present invention relates to an electronic device, such as a miniaturized electronic device. An example of such a device would be an in-vivo medical electronic device, such as a pacemaker.

BACKGROUND OF THE INVENTION

In miniaturised electronic equipment, such as an implantable medical device, space is frequently at a premium, and the use of the minimum number of components is desirable. Another requirement arising in such devices is low power consumption, so the use of an efficient power management techniques is required.

Communication with the in-vivo device maybe by a number of means, such as radio, typified by the Medical Implant Communications Service described in the ITU-R Recommendation SA 1346, typified by equipment meeting the requirements of the Standard EN301 839, or by inductive loop methods, typified by equipment meeting the requirements of the Standards EN300 330 and EN302 195, said Standards being published by the European Telecommunications Standards Institute.

SUMMARY OF THE INVENTION

In accordance with the invention an inductor, or pick up coil, in the power management circuitry of an electronic device can also be used to receive a predominantly inductive field (such as that defined in the Standard EN 300 330) transmitted for the purposes of communicating with the device. By suitable use of radio access protocols combined with power management protocols, the power converter can be switched off during periods of communication reception, and vice versa. In this way, the inductor can be switched between a communication mode and a power conversion mode.

Frequencies used for this communication may conveniently be, but are not restricted to, those frequencies designated by the International Telecommunications Union Radio Regulations as ISM (Industrial, Scientific and Medical) frequencies.

In one embodiment, the device may be an in-vivo medical electronic apparatus in an animal or human.

Thus, according to one aspect, the invention provides an electronic device, comprising a switching regulator power converter for converting energy extracted from a power source to powering the device; an inductive element configured to function in a communication mode as an antenna for picking up communication signals, and in a power conversion mode as an inductive element of the switching regulator power conversion circuit; a receiver for receiving said communications signals; and a controllable switch for switching between said communication mode and said power conversion mode.

The internal power source is to be understood to mean a power source physically contained within the equipment housing, or alternatively, physically separated from the equipment housing but physically connected to the system by means of an electrical or other cable, for example, by an optical fibre used either incidentally or solely for the purpose of conveying power to the system.

The controllable switch may switch can comprise unipolar or bipolar transistor switches or mechanical switches or relays.

The electronic device may also further comprise a capacitor which, in the communication mode, is parallel with the inductive element. The inductor may be resonant at the communications frequency.

There are many advantages in using a multiplexed loop antenna as both the antenna for a communication purpose and the inductive element in a small communications device. First, double use of a single component reduces the total number of components required in the device, thus improving space issues within the device. Second, power consumption of the device is more efficient and streamlined.

Other aspects and advantages of embodiments of the invention will be readily apparent to those ordinarily skilled in the art upon a review of the following description.

BRIEF DESCRIPTION OF THE DRAWINGS

The invention will now be described in more detail, by way of example only, with reference to the accompanying drawings, in which.

DETAILED DESCRIPTION OF THE PREFERRED EMBODIMENTS

Figure 1:
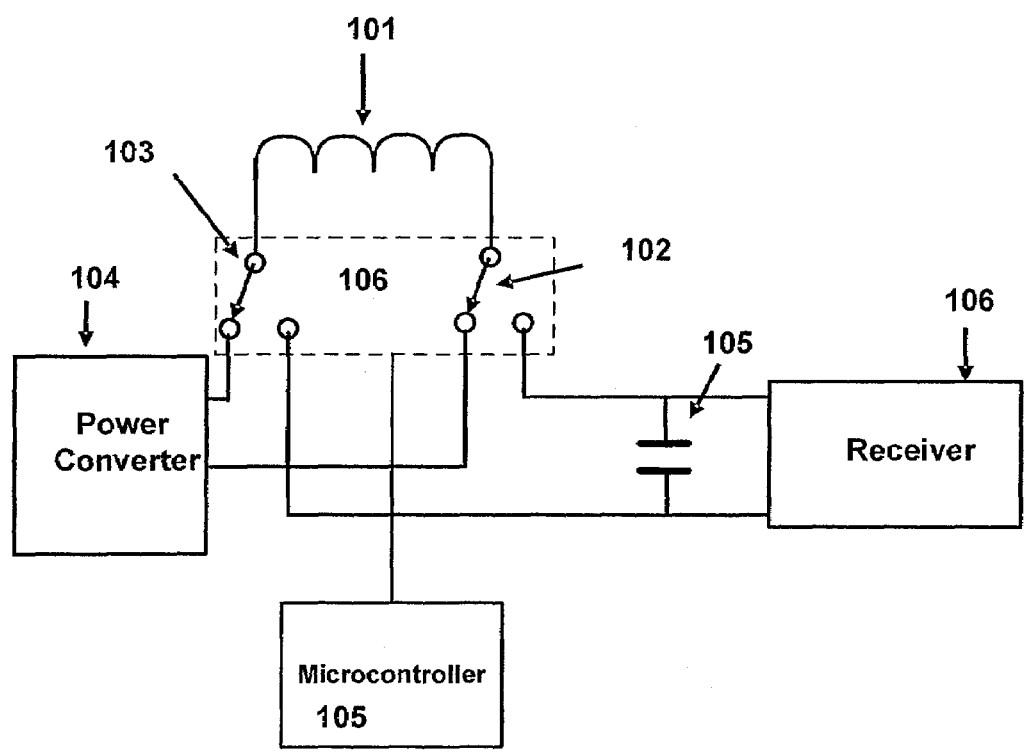
FIG. 1 is a block diagram of a an electronic device with an inductive pick-up element.

The electronic device shown in FIG. 1 can, for example, be an in-vivo medical electronic device located in-vivo in an animal or human, where communication with the device for the purpose of telemetry or telecommand is required. The device receives communications signals from an external source (not shown) and draws its power inductively from an internal power source.

The electronic device includes a dual purpose inductor 101, which serves as an antenna for communications purposes in the communications mode and as an inductive element for power conversion purposes in the power conversion mode. In this mode the inductor 101 is connected to an internal power source so that the power converter 104 can convert energy from the internal-source to power the communications system 100. The power converter can be a 'Buck' or 'Boost' type converter. 'Buck' converters are used for reducing the voltage, while 'Boost' converters are used for increasing voltages. These converters use an inductor as an energy storage device, and are commonly known to those skilled in the art as switching regulators.

During reception of communications signal by the device, the power converter 104 is normally switched off, and the inductor 101, which also serves as an energy storage device, is connected to a receiver 106 to function as an antenna for communications purposes.

In the communication mode, the inductor 101 picks up electromagnetic energy from the external source.

Switch unit 106 comprising switches 102 and 103 serves to connect the inductor 101 to either the power converter 104, or the receiver 106. A microcontroller 105 controlling the switches 102 and 103 connects the switches according to the requirements of allowable latency and the length of the messages to be received, and the overall power requirements of the circuitry fed from the power converter 104. The switches may be actuated on a regular time multiplexed basis, or irregularly as a result of telecommand signals received, or as commanded by another system, for example a microcontroller.

The switches 102 and 103 may be unipolar or bipolar transistors. Desirably, they show a very low resistance in the 'ON' state, and low capacitance in the OFF state. Switches 102 and 103 may also be mechanical switches or relays.

The operational frequency of power converter 104 is chosen with regard to the ratio of the input to output voltage of the converter, the desired efficiency, the possibilities of interference with other circuitry in close proximity to the converter, and the available values of inductance in physical sizes consistent with the application. A typical frequency could be in the 1 to 2 MHz region.

The operational frequency of receiver 106 is chosen with regard to the value of inductor required by the converter 104, the radiated power level allowed (in this respect, it should be noted that in general, the radiated power allowed at the ISM frequencies is higher than at other frequencies) and the available values of inductance in physical sizes consistent with the application. Typical frequencies for such use are 6.78, 13.56 and 27.12 MHz.

Capacitor 105 may not always be needed, although the received signal will be greater when the circuit consisting of the inductor 101 and the capacitor 105 is resonant. However, such resonance is not necessary for the system contemplated by the invention to work.

In the case that the capacitor 105 is used, the value of inductor 101 is chosen to provide both the correct inductance value for the power converter 104 requirements, and to resonate with the capacitor 105 at the frequency at which it is required to receive a signal. The sensitivity of the receiving system is proportional to the physical size of the inductor, but radiation from the inductor when being used in the power conversion circuitry can also be increased, although in that case difficulties in meeting requirements on emissions covered by EMC (Electro Magnetic Compatibility) requirements may be experienced.

Numerous modifications may be made without departing from the spirit and scope of the invention as defined in the appended claims.

What is claimed is:

1. An in-vivo electronic device, comprising:
  a switching regulator power converter selected from the group consisting of a Buck converter and a Boost converter for converting energy extracted from a power source to powering the device having a first pair of terminals;
  a common inductive element configured to function in a communication mode as an antenna for inductively picking up communication signals, and in a power conversion mode as an inductive element of the switching regulator power conversion, said inductive element having a second pair of terminals;
  a receiver for receiving said inductively picked up communications signals having a third pair of terminals;
  a controllable switch for switching respective terminals of said first pair of terminals between corresponding terminals of said second pair of terminals and said third pair of terminals on a time-multiplexed basis to change between said communication mode and said power conversion mode; and
  a microcontroller for controlling said switch to select said second pair of terminals or said third pair of terminals according to the requirements of latency and length of the messages to be received.

2. An electronic device as claimed in claim 1, wherein the controllable switch comprises unipolar or bipolar transistor switches or mechanical switches or relays.

3. An electronic device as claimed in claim 1, wherein a capacitor is connected between said third pair of terminals, said capacitor having a value selected to form a resonant circuit with said inductor when said respective terminals of said first pair of terminals are connected to said corresponding terminals of said third pair of terminals.

* * * * *